US00PP32689P2

(12) United States Plant Patent
Danziger

(10) Patent No.: US PP32,689 P2
(45) Date of Patent: Dec. 22, 2020

(54) ***SCAEVOLA* PLANT NAMED 'DSCAWINDST'**

(50) Latin Name: *Scaevola aemula*
Varietal Denomination: DSCAWINDST

(71) Applicant: Gavriel Danziger, Moshav Mishmar Hashiva (IL)

(72) Inventor: Gavriel Danziger, Moshav Mishmar Hashiva (IL)

(73) Assignee: DANZIGER "DAN" FLOWER FARM, Beit Dagan (IL)

( * ) Notice: Subject to any disclaimer, the term of this patent is extended or adjusted under 35 U.S.C. 154(b) by 0 days.

(21) Appl. No.: 16/873,548

(22) Filed: Apr. 30, 2020

(51) Int. Cl.
*A01H 5/02* (2018.01)
*A01H 6/00* (2018.01)

(52) U.S. Cl.
USPC ..... Plt./363

(58) Field of Classification Search
USPC ..... Plt./263.1, 363
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Scaevola* plant named 'DSCAWINDST', characterized by its outwardly spreading and mounded plant habit; freely branching habit; relatively broad leaves; early and freely flowering habit; white and purplish blue bi-colored flowers; and good container and garden performance.

2 Drawing Sheets

Figure 1:
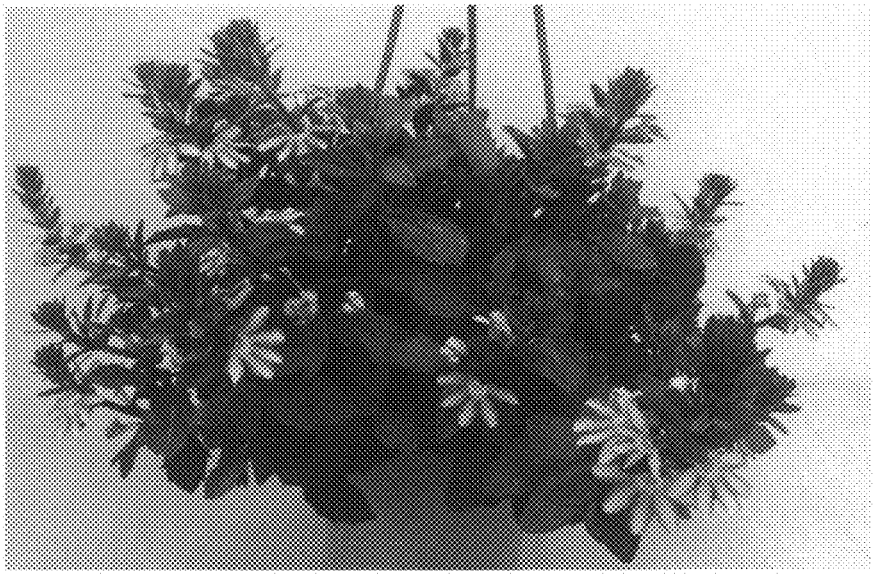

Botanical designation: *Scaevola aemula.*
Cultivar denomination: 'DSCAWINDST'.

BACKGROUND OF THE INVENTION

The present invention relates to a new and distinct cultivar of *Scaevola* plant, botanically known as *Scaevola aemula* and hereinafter referred to by the name 'DSCAWINDST'.

The new *Scaevola* plant a product of a planned breeding program conducted by the Inventor in Mishmar Hashiva, Israel. The objective of the breeding program is to create new compact, spreading and early-flowering *Scaevola* plants with numerous attractive bi-colored flowers.

The new *Scaevola* plant originated from an open-pollination in Mishmar Hashiva, Israel in March, 2015 of a proprietary selection of *Scaevola aemula* identified by the code number 14-1050, not patented, as the female, or seed, parent with an unknown proprietary selection of *Scaevola aemula*, as the male, or pollen, parent. The new *Scaevola* plant was discovered and selected by the Inventor as a single flowering plant from within the progeny of the stated open-pollination in a controlled greenhouse environment in Mishmar Hashiva, Israel on Mar. 15, 2016.

Asexual reproduction of the new *Scaevola* plant by vegetative tip cuttings in a controlled greenhouse environment in Mishmar Hashiva, Israel since Mar. 15, 2016 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DSCAWINDST'. These characteristics in combination distinguish 'DSCAWINDST' as a new and distinct *Scaevola* plant:

1. Outwardly spreading and mounded plant habit.
2. Freely branching habit.
3. Relatively broad leaves.
4. Early and freely flowering habit.
5. White and purplish blue bi-colored flowers.
6. Good container and garden performance.

Plants of the new *Scaevola* can be compared to plants of the female parent selection. Plants of the new *Scaevola* differ primarily from plants of the female parent selection in the following characteristics:

1. Plants of the new *Scaevola* are more vigorous than and not as compact as plants of the female parent selection.
2. Plants of the new *Scaevola* have darker leaves than plants of the female parent selection.
3. Plants of the new *Scaevola* and the female parent selection differ in flower color as plants of the new *Scaevola* have white and purplish blue bi-colored flowers whereas plants of the female parent selection have lavender-colored flowers.

Plants of the new *Scaevola* can be compared to plants of the *Scaevola aemula* 'Wesscaedia', disclosed in U.S. Plant Pat. No. 15,431. In side-by-side comparisons, plants of the new *Scaevola* differ from plants of the 'Wesscaedia' in the following characteristics:

1. Plants of the new *Scaevola* are more mounding than and not as trailing as plants of 'Wesscaedia'.
2. Plants of the new *Scaevola* have shorter internodes than plants of 'Wesscaedia'.
3. Plants of the new *Scaevola* flower earlier than plants of 'Wesscaedia'.

Plants of the new *Scaevola* can also be compared to plants of the *Scaevola aemula* 'Brillant', disclosed in U.S. Plant Pat. No. 12,099. In side-by-side comparisons, plants of the new *Scaevola* differ from plants of the 'Brillant' in the following characteristics:

1. Plants of the new *Scaevola* are more mounding than and not as trailing as plants of 'Brillant'.
2. Plants of the new *Scaevola* are not as vigorous as plants of 'Brillant'.
3. Plants of the new *Scaevola* have smaller flowers than plants of 'Brillant'.
4. Plants of the new *Scaevola* and 'Brillant' differ in flower color as plants of the new *Scaevola* have white and purplish blue bi-colored flowers whereas plants of 'Brillant' have blue purple-colored flowers.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph on the first sheet (FIG. 1 of 2) is a side perspective view of a typical flowering plant of 'DSCAW-INDST' grown in a container.

Figure 2:
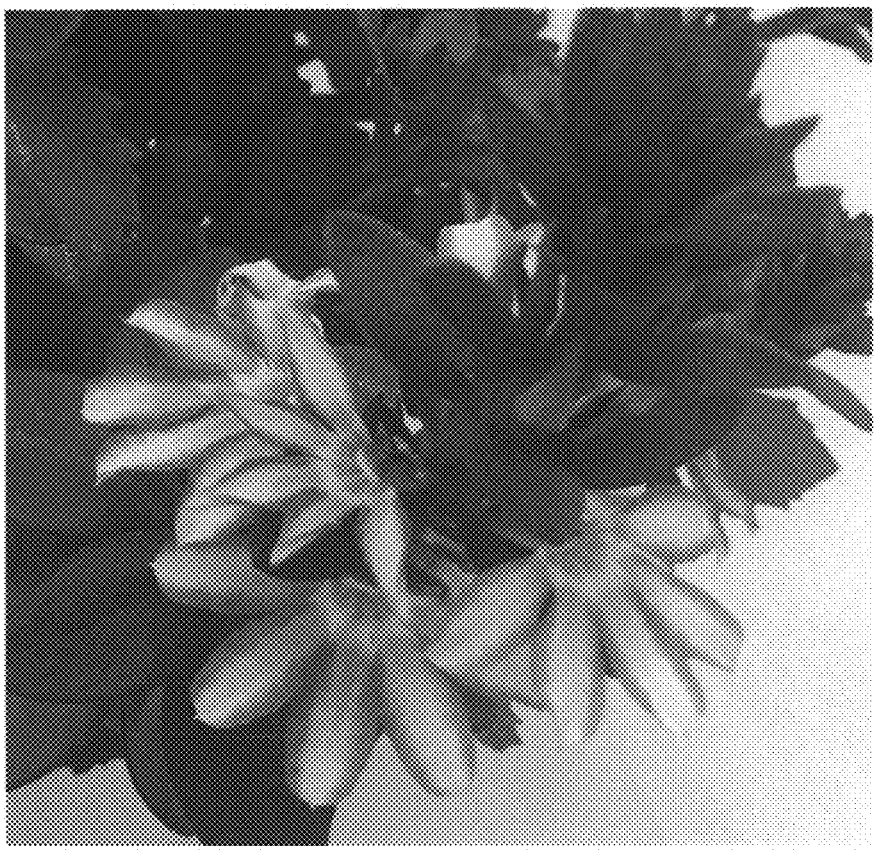

The photograph on the second sheet (FIG. 2 of 2) is a close-up view of a typical flowering plant of 'DSCAW-INDST'.

DETAILED BOTANICAL DESCRIPTION

The aforementioned photographs and following observations, measurements and values describe plants grown during the summer in 13-cm containers in a greenhouse and finished in an outdoor nursery in Mishmar Hashiva, Israel and under cultural practices typical of commercial *Scaevola* production. During the production of the plants, day temperatures ranged from 15° C. to 28° C. and night temperatures ranged from 10° C. to 15° C. Plants were eight weeks old when the photographs and the detailed description were taken. In the following description, color references are made to The Royal Horticultural Society Colour Chart, 2007 Edition, except where general terms of ordinary dictionary significance are used.

Botanical classification: *Scaevola aemula* 'DSCAW-INDST'.

Parentage:

*Female, or seed, parent*.—Proprietary selection of *Scaevola aemula* identified as code number 14-1050, not patented.

*Male or pollen parent*.—Unknown proprietary selection of *Scaevola aemula*, not patented.

Propagation:

*Type*.—By vegetative tip cuttings.

*Time to initiate roots, summer*.—About 14 to 21 days at temperatures about 30° C.

*Time to initiate roots, winter*.—About 21 to 30 days at temperatures about 16° C. to 20° C.

*Time to produce a rooted young plant, summer*.—About 30 to 40 days at temperatures about 30° C.

*Time to produce a rooted young plant, winter*.—About 40 to 50 days at temperatures about 16° C. to 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Outwardly spreading and mounding plant habit; moderately vigorous growth habit.

*Branching habit*.—Freely branching habit with about 25 lateral branches per plant.

*Plant height*.—About 15 cm.

*Plant diameter* (*area of spread*).—About 45 cm.

Lateral branch description:

*Length*.—About 20 cm to 23 cm.

*Diameter*.—About 6 mm.

*Internode length*.—About 1.5 cm.

*Aspect*.—Upright to outwardly.

*Texture*.—Pilose.

*Color*.—Close to 146B becoming closer to 200B with development.

Leaf description:

*Arrangement*.—Alternate, simple.

*Length*.—About 5 cm.

*Width*.—About 2.5 cm.

*Shape*.—Runcinate.

*Apex*.—Blunt or emarginate.

*Base*.—Cuneate.

*Margin*.—Dentate.

*Texture, upper surface*.—Hispid; rugged.

*Texture, lower surface*.—Pilose; rugged.

*Venation pattern*.—Pinnate, reticulate.

*Color*.—Developing leaves, upper surface: Close to 137A. Developing leaves, lower surface: Close to 137C. Fully expanded leaves, upper surface: Close to 137B; venation, close to 138B. Fully expanded leaves, lower surface: Close to 137C; venation, close to 138B.

*Petioles*.—Length: About 1 cm. Diameter: About 3 mm to 4 mm. Texture: Hispid; rugged. Color: Close to 138B.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about 150 flowers per plant.

*Flowering time*.—Early flowering habit, plants begin flowering after about four to six weeks after planting; long flowering period, plants flower continuously from spring to autumn in Israel.

*Flower longevity*.—Flowers typically last about 20 days on the plant; flowers not persistent.

*Fragrance*.—None detected.

*Flower buds*.—Length: About 1.5 cm. Diameter: About 4 mm. Shape: Fusiform. Color: Close to 142C.

*Flowers*.—Diameter: About 3 cm by 2 cm. Tube length: About 1.2 cm. Tube diameter: About 5 mm.

*Petals*.—Quantity per flower: Five, fused at base. Length, beyond tube: About 1.3 cm. Width, beyond tube: About 4 mm. Shape: Oblong. Apex: Cuspidate. Margin: Entire. Texture, upper and lower surfaces:

Smooth, glabrous; velvety. Color: When opening, upper surface: Center, close to NN155B; towards the margins, close to 93C. When opening, lower surface: Center, close to 2D and 155B; towards the margins, close to 93C. Fully opened, upper surface: Center, close to 155C; towards the margins, close to 94C; color does not change with development. Fully opened, lower surface: Center, close to 2D and 155C; towards the margins, close to 94B; with development, color towards the margins becoming closer to 94C. Throat: Close to N144A; becoming closer to 2B to 2C with development. Tube: Close to 2C; becoming closer to 2D with development.

*Sepals*.—Quantity per flower: Two short and one elongated. Length, short sepals: About 7 mm. Length, elongated sepal: About 2 cm. Width, short sepals: About 2 mm. Width, elongated sepal: About 9 mm. Shape: Ligulate. Apex: Acute. Base: Fused. Margin: Entire. Texture, upper and lower surfaces: Hispid, rugged. Color, upper and lower surfaces: Close to 147A to 147B.

*Reproductive organs*.—Androecium: Stamen quantity per flower: Five. Filament length: About 4 mm. Filament color: Close to 2C. Anther length: About 1.5 mm. Anther shape: Ellipsoidal. Anther color: Close to 183A. Pollen: Scarce. Pollen color: Close to 9D. Gynoecium: Pistil quantity per flower: One. Pistil length: About 1.5 cm. Style length: About 1 cm. Style color: Close to 187A. Stigma shape: Oblate. Stigma color: Close to 183D. Ovary color: Close to 138B.

*Seeds*.—Quantity per flower: One. Length: About 4 mm. Diameter: About 2 mm. Color: Close to 202A.

Garden performance: Plants of the new *Scaevola* have been observed to have good garden performance and to tolerate rain, wind and temperatures ranging from about 5° C. to about 45° C.

Pathogen & pest resistance: To date, plants of the new *Scaevola* have not been shown to be resistant to pathogens and pests common to *Scaevola* plants.

It is claimed:

1. A new and distinct *Scaevola* plant named 'DSCAW-INDST' as illustrated and described.

* * * * *